United States Patent
Kirkegaard

(10) Patent No.: US 7,410,058 B2
(45) Date of Patent: Aug. 12, 2008

(54) DEVICE ADAPTED FOR KEEPING IN A WALLET, A POCKET, A BAG, OR A SIMILAR PLACE

(75) Inventor: Per Kirkegaard, Skanderborg (DK)

(73) Assignee: Safecard ApS, Skanderborg (DK)

( * ) Notice: Subject to any disclaimer, the term of this patent is extended or adjusted under 35 U.S.C. 154(b) by 298 days.

(21) Appl. No.: 10/798,325

(22) Filed: Mar. 12, 2004

(65) Prior Publication Data

US 2004/0231687 A1 Nov. 25, 2004

Related U.S. Application Data

(63) Continuation of application No. PCT/DK02/00598, filed on Sep. 13, 2002.

(51) Int. Cl.
*B65D 69/00* (2006.01)

(52) U.S. Cl. .................. 206/570; 206/38; 606/131

(58) Field of Classification Search .............. 206/38, 206/438, 440, 570; 606/131; 473/408; D24/127, D24/133; 132/75.6
See application file for complete search history.

(56) References Cited

U.S. PATENT DOCUMENTS

| | | | |
|---|---|---|---|
| 3,534,887 A | 10/1970 | Ginsberg | |
| 4,063,731 A * | 12/1977 | Kitay | ............... 473/286 |
| 4,220,244 A | 9/1980 | Elmore | |
| 4,301,923 A | 11/1981 | Vuorento | |
| 4,513,842 A * | 4/1985 | Karlsberg | ............... 132/149 |
| 4,900,663 A | 2/1990 | Wie et al. | |
| 4,938,764 A | 7/1990 | Glaberson | |
| 4,946,033 A | 8/1990 | Conner | |
| 4,976,718 A | 12/1990 | Daniell | |
| 5,002,323 A | 3/1991 | Idsund | |
| 5,078,729 A | 1/1992 | Eichhorn | |
| 5,116,347 A | 5/1992 | Butler | |
| 5,246,449 A | 9/1993 | Webster | |
| D353,002 S | 11/1994 | Tovey | |
| 5,447,511 A * | 9/1995 | Gadd | ............... 606/131 |
| 5,595,569 A | 1/1997 | Hebbard | |
| 5,607,434 A * | 3/1997 | Alvino | ............... 606/131 |
| 5,645,500 A * | 7/1997 | Borden | ............... 473/408 |

(Continued)

FOREIGN PATENT DOCUMENTS

| | | |
|---|---|---|
| CA | 2152117 | 6/1995 |
| DE | 27 17 128 | 11/1978 |
| DE | 297 22 310 | 4/1998 |
| FR | 2 791 326 | 3/1999 |

*Primary Examiner*—David T Fidei
(74) *Attorney, Agent, or Firm*—Antonelli, Terry, Stout & Kraus, LLP.

(57) ABSTRACT

A device adapted for keeping in a wallet, a pocket, a bag, or a similar place, said device is designed as a credit card in size and preferably has a display surface intended for commercial use, where said device is made of a relative stiff material such as cardboard or plastic, and that said device in a corner area is provided with a flexible finger (46), which at an outer end (48) is provided with a slit or narrowing (50) for use in removing a tick or corresponding blood sucking insect, which has bitten on to and bored its snout down into the skin of a person or an animal.

20 Claims, 1 Drawing Sheet

U.S. PATENT DOCUMENTS

Figure 1:
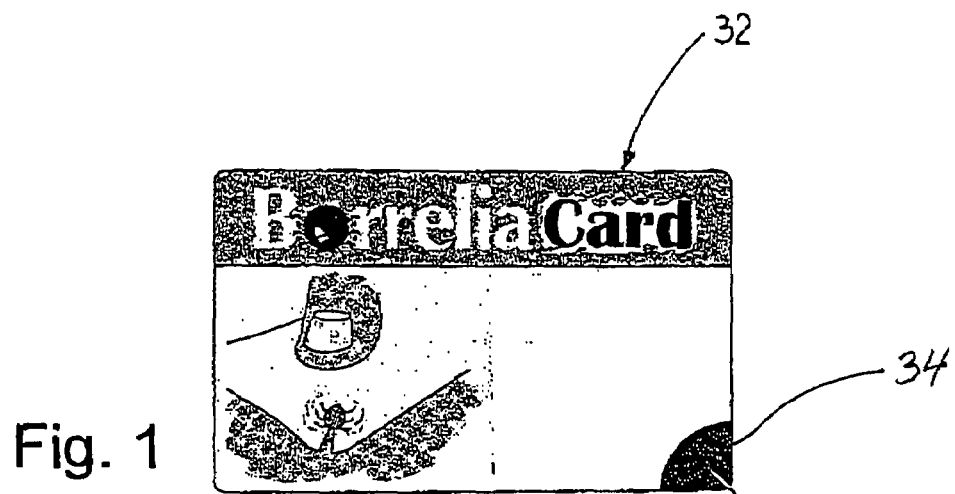

| | | | |
|---|---|---|---|
| 5,704,847 A * | 1/1998 | Glennon | 473/282 |
| 5,787,907 A | 8/1998 | Endelson | |
| 5,876,409 A | 3/1999 | Heitz | |
| 5,911,319 A | 6/1999 | Porcelli et al. | |
| 6,076,661 A | 6/2000 | Abadi | |
| 6,102,919 A | 8/2000 | Licata | |

* cited by examiner

DEVICE ADAPTED FOR KEEPING IN A WALLET, A POCKET, A BAG, OR A SIMILAR PLACE

CROSS REFERENCE TO RELATED APPLICATION

This application is a continuation of PCT/DK02/00598, filed Sep. 13, 2002, and entitled "A Device By Way of Example for Personal Hygiene", the subject matter of which is incorporated by reference herein by reference in its entirety.

BACKGROUND OF THE INVENTION

1. Field of the Invention

The present invention concerns a device for keeping in a wallet, a pocket, a bag or a similar place.

2. Description of the Prior Art

Arrangements of that kind are known by way of example as small disposable packings, most often in the form of tear-open bags of plastic or metal film containing a folded wet tissue for cleaning hands and/or face. In connection with car wash in automatic facilities on service stations it is also known that corresponding tear-open bags of plastic or metal film containing prepared tissue for use in cleaning wax from the windshield for the car are handed out. In some cases, a number of cohering tear-up bags are handed out, which are intended to be separated by means of perforations, and which may contain tissues prepared with different cleaning agents and possibly a dry tissue for final wiping of the windshield of the car.

BRIEF SUMMARY OF THE INVENTION

On this background, it is the purpose of the invention to provide a new and improved device and which in a simple way makes it possible for persons to carry with one or more devices with the intention of removing a tick or a similar blood sucking insect.

The device according to the invention is made of a relatively stiff material such as cardboard or plastic, and that the device in a corner area is provided with a flexible finger, which at an outer end is provided with a slit or narrowing for use in removing a tick or corresponding blood sucking insect, which has bitten on to and bored its snout down into the skin of a person or an animal. The device according to the invention may be manufactured and distributed very cheaply as the device may be partly financed by commercial advertisements due to the preferable display surface.

Suitably, the device according to the invention is thus designed, that another corner area is also provided with a mainly acute angled slit or narrowing adapted for use in releasing a tick or a similar insect.

Preferably, the device according to the invention is thus designed so that the cleaning tissue preferably has a size which is greater than that of the carrier or reservoir.

Suitably, the device is further designed so that the cover films are provided with a corner or tongue section, which is not connected with the device, and which is intended for use in pulling off the cover films.

It may be further advantageous that the device is made with a preferably transverse perforation extending between the tissue and the carrier or reservoir, respectively, and which are intended as aid for dividing the device into a part containing a covered tissue and a part containing a covered carrier or a covered reservoir, respectively.

Furthermore the device according to the invention may be such provided, that it on one side has two film covered fields, namely a field in which is laid a disinfecting tissue and a field in which is laid a plaster, and that the fields externally are covered by means of one or more cover film pieces consisting of preferably easily removable (peel-able) plastic or metal film.

The invention is explained in the following in more detail in connection with the drawing, on which:

BRIEF DESCRIPTION OF THE SEVERAL VIEWS OF THE DRAWNGS

Figure 2:
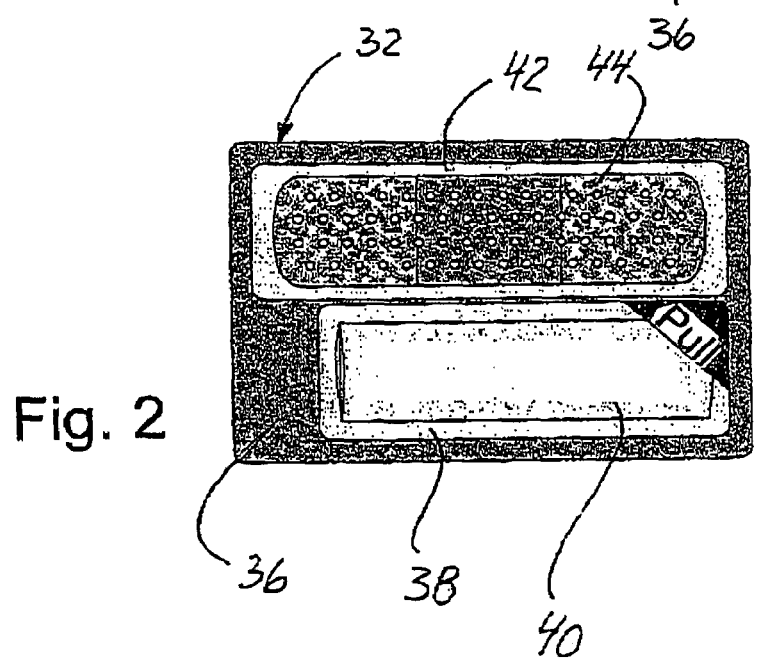
Figure 3:
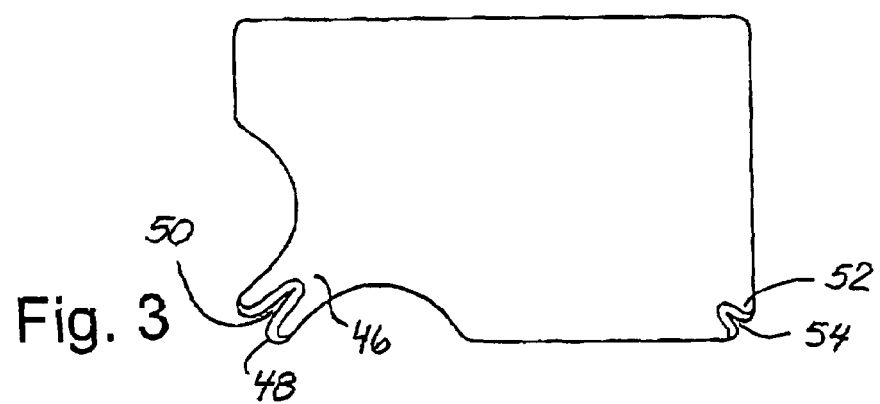

FIG. 1 shows the front side of an embodiment of a device according to the invention in a shape of a "BorreliaCard" for use in releasing a tick, FIG. 2 shows the back side of the "BorreliaCard" shown in FIG. 1, and FIG. 3 shows a preferred embodiment of a "BorreliaCard" according to the invention.

DETAILED DESCRIPTION OF THE INVENTION

As mentioned, the device according to the invention preferably has a size corresponding to a credit card, that is designed with rounded corners with a length of about or substantially 85 mm, a width of about or substantially 54 mm and a total thickness less than 4 mm, preferably less than 2 mm.

The "BorreliaCard" 32 shown in FIGS. 1 and 2 has a corner area 34 designed with an acutely angled slit or cut-out 36 adapted for use in removing a tick or similar blood sucking insects that has bitten onto and bored down into the skin of a person or an animal, by way of example a dog.

The card 32 is by way of example printed with the following instructions on the front side:

STOP the TICK!

Place the slit of the Borrelia card under the tick's abdomen as close to the skin as possible Push the card forward so that the tick is lifted out calmly and firmly Treat subsequently with chlorhexidine and possibly plaster or adhesive bandage The disclosed slit or cut-out 36, which may end up in a circular hole, may alternatively, or as a supplement, also be provided at a short side of the card. The "BorreliaCard" will hereby act as a pre-stressed spring which by itself, after placing under and around the tick, will provide a certain pulling or elevation action on the tick so that it, including mouth parts, will be pulled or lifted off the skin. According to another alternative embodiment, the "BorreliaCard" may be designed with a hole with the shape as a keyhole or other suitable profile which makes it possible to move the card down over the tick and to wedge it in a narrowing of the hole.

At the back side of the card 32 (FIG. 5) there are two film covered fields, namely a field 38 in which is laid a disinfecting cleaning tissue 40 moistened with chlorhexidine, (solution 0.05%), and a field 42 in which laid a piece of plaster 44 or adhesive bandage.

A preferred embodiment of a "BorreliaCard" is shown in FIG. 3, where a corner area is provided with a flexible finger 46, which at an outer end 48 is provided with a slit or narrowing 50 for use in removing a tick or corresponding blood sucking insect. The flexible finger 46 contributes to optimizing the function of the "BorreliaCard", so that one gets hold of the tick with certainty. Besides, the "BorreliaCard", shown in FIG. 3, is at another corner 52 provided with a supplementing smaller slit or narrowing 54.

The preferred embodiment of a "BorreliaCard" shown in FIG. 3 is made of relatively thin plastic material which is preferably without printed instructions, as the "BorreliaCard" in this form preferably is intended to be laid into a folded, card-like brochure or guidance for use, which is finally sealed in a transparent plastic packing, and which furthermore may contain a number of individually packed cleaning tissues and/or a number of individually packed plasters or adhesive bandages.

The invention claimed is:

1. A card comprising:
   first and second planar surfaces, the surfaces including dimensions corresponding to a credit card, being parallel to each other, being separated by a distance of less than 4 mm, a length of substantially 85 mm, a width of substantially 54 mm and corner areas located at an intersection of the length and the width of the surfaces; and
   a slit located in at least one of the corner areas for use in removing a tick or blood sucking insect, which has bitten into or bored down into the skin of a person or an animal; and
   the card being relatively stiff for permitting removal of the tick or the blood sucking insect with the slit of the card.

2. A card according to claim 1, wherein one of the corner areas includes a flexible finger, with the slit at an outer end, for removing the tick or the blood sucking insect.

3. A card according to claim 2, wherein one of the corner areas, includes the slit for removing the tick or the blood sucking insect, and another of the corner areas includes a flexible finger, with a slit at an outer end for removing the tick or the blood sucking insect.

4. A card according to claim 1 wherein the card is includes instructions on the first surface for removing the tick or the blood sucking insect.

5. A card according to claim 4 wherein the instructions are also for treating an area from which the tick or the blood sucking insect was removed.

6. A card according to claim 2 wherein the card includes instructions on the first surface for removing the tick or the blood sucking insect.

7. A card according to claim 6 wherein the instructions are also for treating an area from which the tick or the blood sucking insect was removed.

8. A card according to claim 1 wherein the card includes film covered fields on the second surface comprising a field containing a disinfecting tissue and a field containing an adhesive bandage.

9. A card according to claim 2 wherein the card includes film covered fields on the second surface comprising a field containing a disinfecting tissue and a field containing an adhesive bandage.

10. A card comprising:
    first and second planar surfaces, the surfaces including dimensions corresponding to a credit card, being parallel to each other, being separated by a distance of less than 4 mm, a length of substantially 85 mm, a width of substantially 54 mm and corner areas located at an intersection of the length and the width of the surfaces; and
    one of the corner areas of the card including means for removing a tick or a blood sucking insect, which has bitten into or bored down into the skin of a person or an animal, and
    the card being relatively stiff for permitting removal of the tick or the blood sucking insect with the means for removing.

11. A card according to claim 10, wherein the means for removing comprises a slit.

12. A card according to claim 10, wherein the means for removing comprises one of the corner areas with a flexible finger with a slit at an outer end for removing the tick or the blood sucking insect.

13. A card according to claim 11, wherein the means for removing comprises one of the corner areas with a flexible finger with the slit at an outer end for removing the tick or the blood sucking insect.

14. A card according to claim 10, wherein the card in one of the corner areas, includes a slit for removing the tick or the blood sucking insect, and another of the corner areas includes a flexible finger with a slit at an outer end for removing the tick or the blood sucking insect.

15. A card according to claim 11, wherein the card in one of the corner areas, includes the slit for removing the tick or the blood sucking insect, and another of the corner areas includes flexible finger with a slit at an outer end for removing the tick or the blood sucking insect.

16. A card according to claim 12, wherein the card in one of the corner areas, includes a slit for removing the tick or the blood sucking insect, and another of the corner area includes flexible finger with a slit at an outer end for removing the tick or the blood sucking insect.

17. A card according to claim 10 wherein the card includes instructions on the first surface for removing the tick or the blood sucking insect.

18. A card according to claim 17 wherein the instructions are also for treating an area from which the tick or the blood sucking insect was removed.

19. A card according to claim 10, wherein the card includes film covered fields on the second surface comprising a field containing a disinfecting tissue and a field containing an adhesive bandage.

20. A card according to claim 11, wherein the card includes film covered fields on the second surface comprising a field containing a disinfecting tissue and a field containing an adhesive bandage.

* * * * *